(12) United States Patent
Becker et al.

(10) Patent No.: US 7,501,558 B2
(45) Date of Patent: Mar. 10, 2009

(54) MODIFIED LOW MOLECULAR WEIGHT GLUTENIN GENE IN PLANTS

(75) Inventors: Dirk Becker, Hamburg (DE); Manfred Gahrtz, Hamburg (DE); Horst Lorz, Hamburg (DE); Maren Schroder, Hamburg (DE)

(73) Assignee: Monsanto Agrar Deutschland GmbH, Dusseldorf (DE)

( * ) Notice: Subject to any disclaimer, the term of this patent is extended or adjusted under 35 U.S.C. 154(b) by 125 days.

(21) Appl. No.: 10/548,228

(22) PCT Filed: Mar. 2, 2004

(86) PCT No.: PCT/EP2004/002079

§ 371 (c)(1), (2), (4) Date: Dec. 27, 2005

(87) PCT Pub. No.: WO2004/078982

PCT Pub. Date: Sep. 16, 2004

(65) Prior Publication Data

US 2007/0054400 A1 Mar. 8, 2007

(30) Foreign Application Priority Data

Mar. 3, 2003 (EP) .................................. 03004633

(51) Int. Cl.
*A01H 1/00* (2006.01)
*C07H 21/04* (2006.01)
*C12N 15/00* (2006.01)
*C07K 14/415* (2006.01)

(52) U.S. Cl. ............................ 800/295; 435/6; 435/69.1; 435/468; 435/419; 435/252.3; 435/320.1; 536/23.6; 800/278; 800/320.1; 800/320.3

(58) Field of Classification Search ..................... 435/6, 435/69.1, 468, 419, 252.3, 320.1; 530/370; 536/23.6; 800/278, 295
See application file for complete search history.

(56) References Cited

OTHER PUBLICATIONS

Ikeda T.M. et al, "Low-Molecular Weight Glutenin Subunit Group 8 Type IV", *Database EMBL Online*, XP-002247533, (2002). Database accession No. Q8W3V4.
Ikeda T.M. et al, "Low-Molecular Weight Glutenin Storage Protein", *Database EMBL Online*, XP-002247534, (1997). Database accession No. P93790.
Detlef Schuppan et al., "Gluten and the Gut—Lessons for Immune Regulation", *Science*, 297:2218-2220, (2002).
L. Willemijn Vader et al, "Specificity of Tissue Transglutaminase Explains Cereal Toxicity in Celiac Disease", *J. Exp. Med.*, 195(5):643-649 (2002).
Willemijn Vader et al., "The Gluten Response in Children with Celiac Disease is Directed Toward Multiple Gliadin and Glutenin Peptides", *Gastroenterology*, 122:1729-1737 (2002).
PCT/EP2004/002079 International Search Report dated Aug. 30, 2004.

*Primary Examiner*—Phuong T Bui
(74) *Attorney, Agent, or Firm*—Howrey LLP

(57) ABSTRACT

The present invention relates to transgenic plants, such as wheat or maize, comprising plant cells having SEQ. ID. NO. 1 and seeds derived from those plants. It also relates to the use of said seed for the preparation of a flour which in turn is used for the preparation of food and/or feed such as dough, batters, pastries, cookies, pasta, wafers, bread and/or confectionery. The thus obtained gliadin-free foodstuff is beneficial for feeding patients suffering from coeliac disease and/or other forms of gluten intolerance.

8 Claims, 16 Drawing Sheets

CATATGAAGACCTTCCTCGTCTTTGCCCTTCTAGCCGTTGTGGCGACA
TCTGCCATTGCACAGATGGAGACTAGCATCCCTGGTTTGGAGAGACCATGGCA
GCAACAACCATTACAACAAAAGAGACATTTCCACAACAACCGCCATCTTCACAA
CAACAACAACCATTTCCTCAACAACCACCATTTTTGCAGCAACAACCTTCATTTT
CGCAGCAACCACTATTTTCACAGAAACAACAACCAGTTCTACCACAACAACCAG
CATTTTCGCAGCAACAACAAACAGTTCTACCACAACAACCAGCATTTTCGCAGCA
ACAACACCAACAGCTTCTGCAACAACAAATCCCTATTGTTCATCCATCCATTTTG
CAGCAGCTAAACCCGTGCAAGGTATTCCTCCAGCAGCAGTGTAGCCCTGTGGC
AATGCCACAACATCTTGCTAGGTCGCAGATGTGGCAGCAGAGCAGTTGCAATGT
GATGCAGCAACAATGTTGCCAACAATTGCCACGAATCCCCGAACAATCCCGCTA
TGAGGCAATCCGTGCTATCATCTTCTCCATCATCCTACAAGAACAACAACAGGG
TTTTGTCCAACCTCAGCAGCAACAACCCCAACAGTCGGTTCAAGGTGTCTACCA
ACCCCAACAGCAGTCGCAGCAGCAGCTCGGACAAGGTTCTTTCCAACAACCTCA
ACAACAACTGGGTCAACAACCTCAACAACAACAGGTACAAAAGGGTACCTTTTT
GCAGCCACACCAGATAGCTCGCCTTGAGGTGATGACTTCCATTGCACTCCGTAC
CCTGCCAACGATGTGCAGTGTCAATGTGCCGTTGTACAGCTCCATCACTAGTGC
GCCATTAGGCGTTGGCAGCCGAGTTGGTGCCTACTGATCTAGS

Figure 2.

MKTFLVFALLAVVATSAIAQMETSIPGLERPWQQQPLQQKETFPQQPPSSQQQQPF
PQQPPFLQQQPSFSQQPLFSQKQQPVLPQQPAFSQQQQTVLPQQPAFSQQQHQ
QLLQQQIPIVHPSILQQLNPCKVFLQQQCSPVAMPQHLARSQMWQQSSCNVMQQQ
CCQQLPRIPEQSRYEAIRAIIFSIILQEQQQGFVQPQQQQPQQSVQGVYQPQQQSQ
QQLGQQSFQQPQQQLGQQPQQQQVQKGTFLQPHQIARLEVMTSIALRTLPTMCSV
NVPLYSSITSAPLGVGSRVGAY

Insert of clone pL-Zc2T-2:

GGATCCCCTAGGTACCTGAAGAAACTATGTGCTGTAGTATAGCCGCTGGCTAGCTAGCTAGT
TGAGTCATTTAGCGGCGATGATTGAGTAATAATGTGTCACGCATCACCATGGGTGGCAGTGT
CAGTGTGAGCAATGACCTGAATGAACAATTGAAATGAAAAGAAAAAAGTATTGTTCCAAATT
AAACGTTTTAACCTTTTAATAGGTTTATACAACAATTTATATGTGTGTTTTCTATATATATC
TAGATTTGTTATCATCCATTTGGATATAGACAAAAAAAAATTATAAGAACTAAAACGAATAC
TAATTTGAAATAAAGGGGGTATATATTGGGATAATGTCCATGAGATCCCTCGTAATATCACT
GACATCACACGTGTGCAGTATCACTGATACATGTATTCACATTTGTTCTGCGTAGGCATACC
TAACAATTTTGATCGACTATCAGAAAGTCAACGAAAGTGAGTCGACTCAAAAAAAATGGGTT
GTGGATGAGGCGTTAGGCCCAACTTATGGCAGCCCGATATCCACAATTGCTGGTTTATATAT
AGCTTCGCTGCTATGTCCTTCGCCTCCCTTAGTTAAAGACTTGAAGCGGCCTTAAGGGCCTG
TACA

Figure 6:

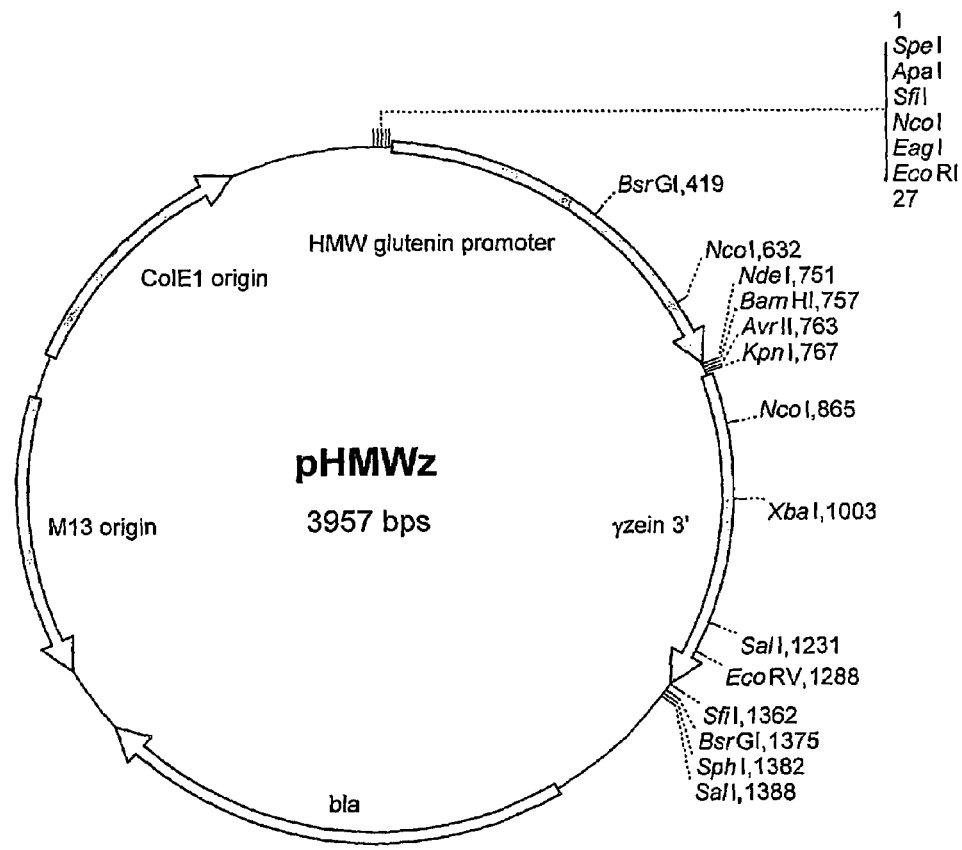

Figure 7:

Insert of clone pHMWz-4:

GGGCCCGGCCATGGCGGCCGAATTCGATCCTATATTAATTTTAGACATGACGGCCAAAGGTT
TCAGTTAGTTCATTTGTCACGGAAAGGTGTTTTCATAAGTCCAAAACTCTACCAACTTTTTT
GCACGTCATAGCATAGATAGATGTTGTGAGTCATTGGATAGATATTGTGAGTCAGCATGGAT
TTGTGTTGCCTGGAAATCCAACTAAATGACAAGCAACAAAACCTGAAATGGGCTTTAGGAGA
GATGGTTCATCAATTTACATGTTCCATGCAGGCTACCTTCCACTACTCGACATGGTAGAAGT
TTTGAGTGCCGCATATTTGCGGAAGCAATGGCTAACAGATACATATTCTGCCAAACCCCTAG
AAGGATAATCACTCCTCTTAGATAAAAAGAACAGACCAATGTACAAACATCCACACTTCTGC
AAACAATACACCAGAACTAGGATTAAGCCCATTACGTGGCTTTAGCAGACCGTCCAAAAATC
TGTTTTGCAAGCACCAATTGCTCCTTACTTATCCAGCTTCTTTTGTGTTGGCAAACTGCCCT
TCTCCAACCGATTTTGTTCTTCTCGCGCTTTCTTCTTAGGCTAAACAGACCTCACCGTGCAC
GCAGCCATGGTCCTGAACCTTCACCTCGTCCCTATAAAAGCCTAACCAACCTTCACAATCTT
ATCATCACCCACAACACCGAGCACCACAAACTAGAGATCAATTCACTGATAGTCCACCGAGC
ATATGGATCC

Figure 8:

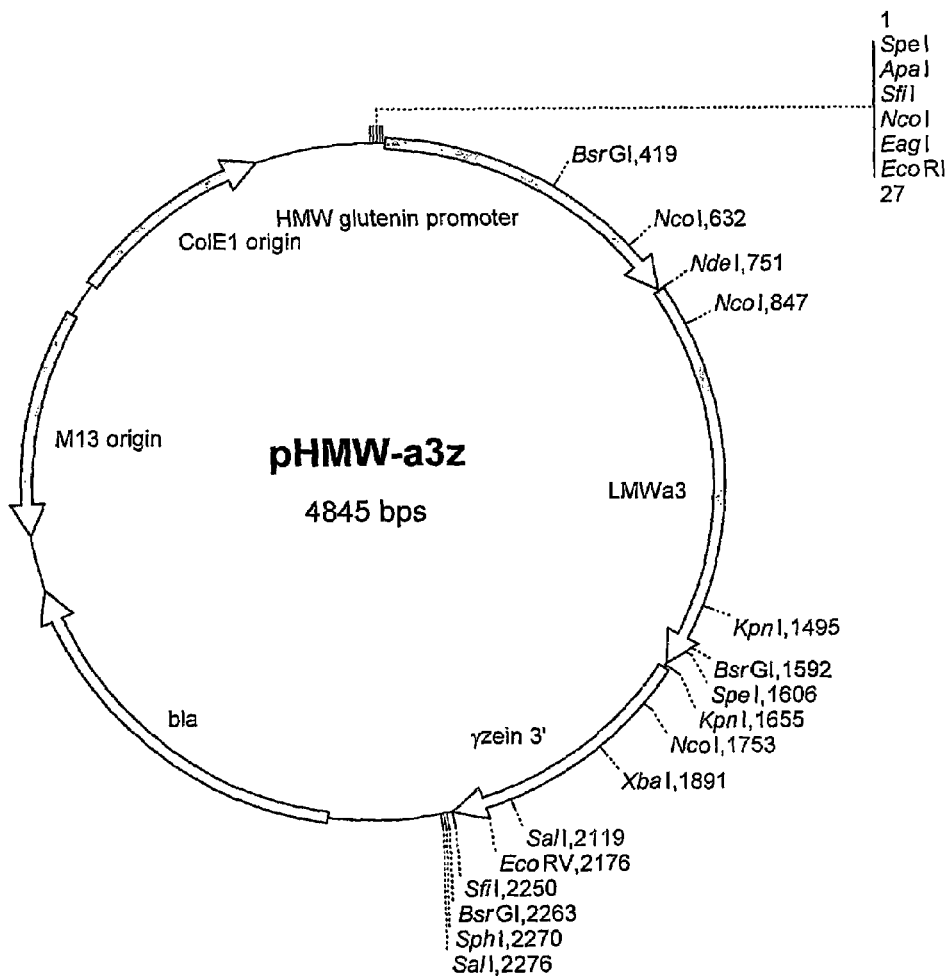

Figure 9:

Insert of clone pHMW-a3z-18:

CATATGAAGACCTTCCTCGTCTTTGCCCTTCTAGCCGTTGTGGCGACATCTGCCATTGCACA
GATGGAGACTAGCTGCATCCCTGGTTTGGAGAGACCATGGCAGCAACAACCATTACAACAAA
AAGAGACATTTCCACAACAACCACCATCTTCACAACAACAACAACCATTTCCTCAACAACCA
CCATTTTTGCAGCAACAACCTTCATTTTCGCAGCAACCACTATTTTCACAGAAACAACAACC
AGTTCTACCACAACAACCAGCATTTTCGCAGCAACAACAAACAGTTCTACCACAACAACCAG
CATTTTCGCAGCAACAACACCAACAGCTTCTGCAACAACAAATCCCTATTGTTCATCCATCC
ATTTTGCAGCAGCTAAACCCGTGCAAGGTATTCCTCCAGCAGCAGTGTAGCCCTGTGGCAAT
GCCACAACATCTTGCTAGGTCGCAGATGTGGCAGCAGAGCAGTTGCAATGTGATGCAGCAAC
AATGTTGCCAACAATTGCCACGAATCCCCGAACAATCCCGCTATGAGGCAATCCGTGCTATC
ATCTTCTCCATCATCCTACAAGAACAACAACAGGGTTTTGTCCAACCTCAGCAGCAACAACC
CCAACAGTCGGTTCAAGGTGTCTACCAACCCCAACAGCAGTCGCAGCAGCAGCTCGGACAAT
GTTCTTTCCAACAACCTCAACAACAACTGGGTCAACAACCTCAACAACAACAGGTACAAAAG
GGTACCTTTTTGCAGCCACACCAGATAGCTCGCCTTGAGGTGATGACTTCCATTGCACTCCG
TACCCTGCCAACGATGTGCAGTGTCAATGTGCCGTTGTACAGCTCCATCACTAGTGCGCCAT
TAGGCGTTGGCAGCCGAGTTGGTGCCTACTGATCTAGG

Figure 10

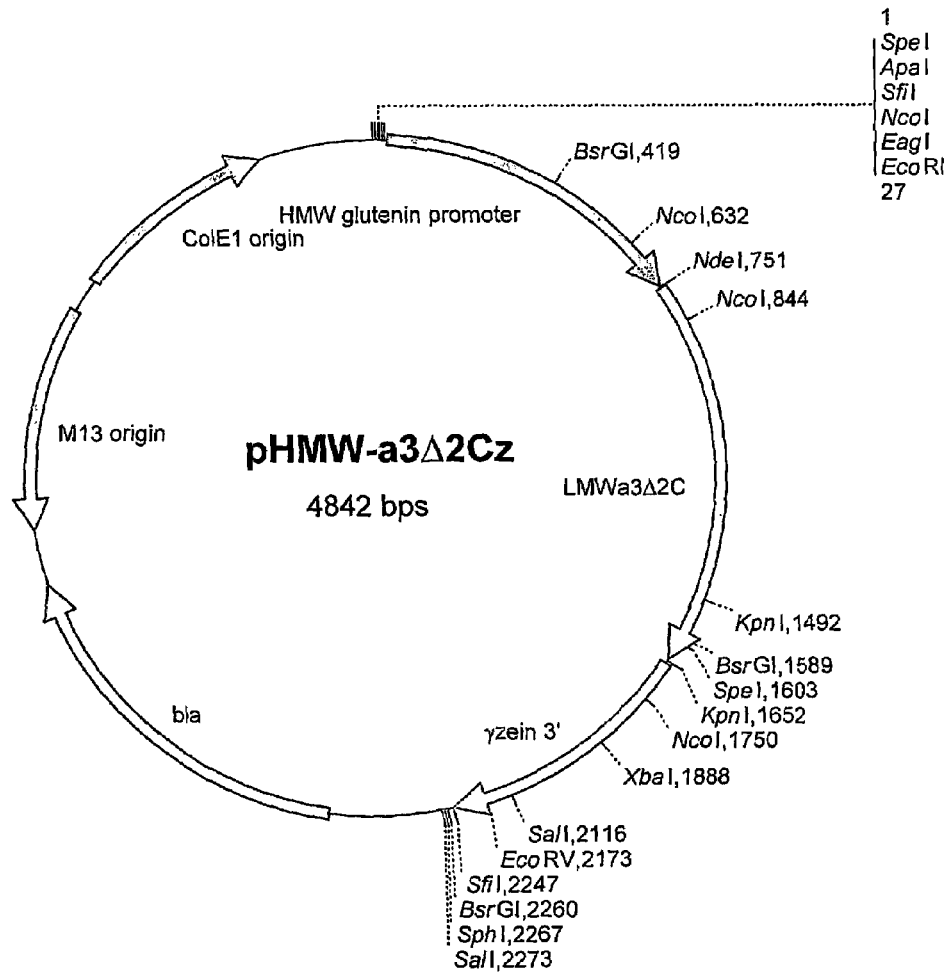

Figure 11:

Insert of clone pHMW-a3Δ2Cz-28:

CATATGAAGACCTTCCTCGTCTTTGCCCTTCTAGCCGTTGTGGCGACATCTGCCATTGCACA
GATGGAGACTAGCATCCCTGGTTTGGAGAGACCATGGCAGCAACAACCATTACAACAAAAAG
AGACATTTCCACAACAACCGCCATCTTCACAACAACAACAACCATTTCCTCAACAACCACCA
TTTTTGCAGCAACAACCTTCATTTTCGCAGCAACCACTATTTTCACAGAAACAACAACCAGT
TCTACCACAACAACCAGCATTTTCGCAGCAACAACAAACAGTTCTACCACAACAACCAGCAT
TTTCGCAGCAACAACACCAACAGCTTCTGCAACAACAAATCCCTATTGTTCATCCATCCATT
TTGCAGCAGCTAAACCCGTGCAAGGTATTCCTCCAGCAGCAGTGTAGCCCTGTGGCAATGCC
ACAACATCTTGCTAGGTCGCAGATGTGGCAGCAGAGCAGTTGCAATGTGATGCAGCAACAAT
GTTGCCAACAATTGCCACGAATCCCCGAACAATCCCGCTATGAGGCAATCCGTGCTATCATC
TTCTCCATCATCCTACAAGAACAACAACAGGGTTTTGTCCAACCTCAGCAGCAACAACCCCA
ACAGTCGGTTCAAGGTGTCTACCAACCCCAACAGCAGTCGCAGCAGCAGCTCGGACAAGGTT
CTTTCCAACAACCTCAACAACAACTGGGTCAACAACCTCAACAACAACAGGTACAAAAGGGT
ACCTTTTTGCAGCCACACCAGATAGCTCGCCTTGAGGTGATGACTTCCATTGCACTCCGTAC
CCTGCCAACGATGTGCAGTGTCAATGTGCCGTTGTACAGCTCCATCACTAGTGCGCCATTAG
GCGTTGGCAGCCGAGTTGGTGCCTACTGATCTAGG

SEQUENCE LISTING

<160> NUMBER OF SEQ ID NOS: 2

<210> SEQ ID NO 1
<211> LENGTH: 903
<212> TYPE: DNA

<213> ORGANISM: Wheat cultivar Cheyenne
<220> FEATURE:
<221> NAME/KEY: gene
<222> LOCATION: (1)..(903)
<223> OTHER INFORMATION: LMWa3DELTAcys2 gene

<400> SEQUENCE: 1

```
catatgaaga ccttcctcgt ctttgccctt ctagccgttg tggcgacatc tgccattgca      60
cagatggaga ctagcatccc tggtttggag agaccatggc agcaacaacc attcaacaa     120
aaagagacat ttccacaaca accgccatct tcacaacaac aacaaccatt tcctcaacaa     180
ccaccatttt tgcagcaaca accttcattt tcgcagcaac cactatttc acagaaacaa     240
caaccagttc taccacaaca accagcattt tcgcagcaac aacaaacagt tctaccacaa     300
caaccagcat tttcgcagca acaacaccaa cagcttctgc aacaacaaat ccctattgtt     360
catccatcca ttttgcagca gctaaacccg tgcaaggtat tcctccagca gcagtgtagc     420
cctgtggcaa tgccacaaca tcttgctagg tcgcagatgt ggcagcagag cagttgcaat     480
gtgatgcagc aacaatgttg ccaacaattg ccacgaatcc ccgaacaatc ccgctatgag     540
gcaatccgtg ctatcatctt ctccatcatc ctacaagaac aacaacaggg ttttgtccaa     600
cctcagcagc aacaacccca acagtcggtt caaggtgtct accaacccca acagcagtcg     660
cagcagcagc tcggacaagg ttcttttccaa caacctcaac aacaactggg tcaacaacct     720
caacaacaac aggtacaaaa gggtaccttt ttgcagccac accagatagc tcgccttgag     780
gtgatgactt ccattgcact ccgtaccctg ccaacgatgt gcagtgtcaa tgtgccgttg     840
tacagctcca tcactagtgc gccattaggc gttggcagcc gagttggtgc ctactgatct     900
agg                                                                  903
```

<210> SEQ ID NO 2
<211> LENGTH: 297
<212> TYPE: PRT
<213> ORGANISM: Wheat cultivar Cheyenne
<220> FEATURE:
<221> NAME/KEY: PEPTIDE
<222> LOCATION: (1)..(297)
<223> OTHER INFORMATION: LMWa3DELTAcys2 peptide

<400> SEQUENCE: 2

```
Met Lys Thr Phe Leu Val Phe Ala Leu Leu Ala Val Val Ala Thr Ser
1               5                   10                  15

Ala Ile Ala Gln Met Glu Thr Ser Ile Pro Gly Leu Glu Arg Pro Trp
            20                  25                  30

Gln Gln Gln Pro Leu Gln Gln Lys Glu Thr Phe Pro Gln Gln Pro Pro
        35                  40                  45

Ser Ser Gln Gln Gln Gln Pro Phe Pro Gln Pro Pro Phe Leu Gln
    50                  55                  60

Gln Gln Pro Ser Phe Ser Gln Gln Pro Leu Phe Ser Gln Lys Gln Gln
65                  70                  75                  80

Pro Val Leu Pro Gln Gln Pro Ala Phe Ser Gln Gln Gln Gln Thr Val
                85                  90                  95

Leu Pro Gln Gln Pro Ala Phe Ser Gln Gln Gln His Gln Gln Leu Leu
            100                 105                 110

Gln Gln Gln Ile Pro Ile Val His Pro Ser Ile Leu Gln Gln Leu Asn
        115                 120                 125

Pro Cys Lys Val Phe Leu Gln Gln Gln Cys Ser Pro Val Ala Met Pro
    130                 135                 140
```

-continued

```
Gln His Leu Ala Arg Ser Gln Met Trp Gln Gln Ser Ser Cys Asn Val
145                 150                 155                 160

Met Gln Gln Gln Cys Cys Gln Gln Leu Pro Arg Ile Pro Glu Gln Ser
                165                 170                 175

Arg Tyr Glu Ala Ile Arg Ala Ile Ile Phe Ser Ile Ile Leu Gln Glu
            180                 185                 190

Gln Gln Gln Gly Phe Val Gln Pro Gln Gln Gln Gln Pro Gln Gln Ser
        195                 200                 205

Val Gln Gly Val Tyr Gln Pro Gln Gln Gln Ser Gln Gln Gln Leu Gly
        210                 215                 220

Gln Gly Ser Phe Gln Gln Pro Gln Gln Gln Leu Gly Gln Gln Pro Gln
225                 230                 235                 240

Gln Gln Gln Val Gln Lys Gly Thr Phe Leu Gln Pro His Gln Ile Ala
                245                 250                 255

Arg Leu Glu Val Met Thr Ser Ile Ala Leu Arg Thr Leu Pro Thr Met
                260                 265                 270

Cys Ser Val Asn Val Pro Leu Tyr Ser Ser Ile Thr Ser Ala Pro Leu
            275                 280                 285

Gly Val Gly Ser Arg Val Gly Ala Tyr
290                 295
```

MODIFIED LOW MOLECULAR WEIGHT GLUTENIN GENE IN PLANTS

This application is a §371 U.S. national stage filing of international application PCT/EP2004/002079, filed 2 Mar. 2004 (published in English on 16 Sep. 2004 as WO 2004/078982) and claiming priority to EP 03004633.8, filed 3 Mar. 2003.

TECHNICAL FIELD

The present invention relates to plants, preferably transgenic plants, such as (transgenic) wheat or maize, comprising a modified low molecular weight glutenin. It also concerns using seed and products thereof which are derived from those plants in the preparation of food and/or feed which is primarily gliadin-free and therefore beneficial for feeding patients suffering from among others coeliac disease and/or other forms of gluten intolerance.

BACKGROUND INFORMATION

Coeliac disease is a condition in which the lining of the small intestine is damaged by gluten, a mixture of different storage proteins found in the starchy endosperm of wheat and rye grains as well as in closely related species. The gluten matrix consists of approximately equal mixtures of gliadin and glutenin proteins. Coeliac disease is primarily caused by the gliadin proteins. Specifically, in this disease the villi of the small intestine are destroyed and the lining becomes flattened, seriously impairing nutrient absorption. Typical symptoms are weight loss, foul-smelling diarrhoe, vomiting, abdominal pain and swelling of the legs. The only cure currently available is a life-long gluten-free diet strictly avoiding all food and pharmaceutical compositions containing wheat, rye and barley.

Further, a number of humans suffer from general intolerance to glutens. The range of intolerance varies greatly although there are no clear clinical symptoms as in coeliac disease. Many humans therefore benefit from reducing the uptake of gluten.

When wheat flour is mixed with water the gluten proteins develop a unique, viscoelastic structure which enables the preparation of a large number of food products. Flour mixed with a small amount of water develops a dough, from which leavened bread, unleavened bread (for example nan, chapattis), biscuits, cookies, and cakes are made in various parts of the world. When a larger amount of water is added to flour, batters are formed and these are used to make wafers, pancakes and other products. Doughs made from durum wheat are used to make cous cous and pasta products: spaghetti, macaroni and the like. In all of these products the gluten matrix traps gas formed during cooking, which allows the developing product to rise/extend through viscous flow and yet maintains the structure (of the product) by developing elastic restraint.

The gliadin proteins comprise a complex mixture of monomeric polypeptides ranging from about 30,000 to 70,000 in molecular weight. The gliadins are often classified into distinct groups, the α/β-, γ- and ω-gliadins.

In contrast, the glutenin proteins have a molecular weight of up to several millions and are among the largest natural polymers known today. They are formed from polypeptide subunits linked via disulphide bonds. The majority of the monomers have a molecular weight which is similar to the gliadins and are called low-molecular-weight (LMW) subunits. The remainder are larger and are referred to as high-molecular-weight (HMW) glutenin subunits. Gliadins and glutenins are conveniently separated by extracting flour with aqueous alcohols, as the gliadins are soluble and the glutenins insoluble under these conditions.

The gliadins impart viscous flow or extensibility to a dough whereas glutenins impart both elasticity and extensibility. The large glutenin molecules contribute more to elasticity and less to extensibility, whereas the smaller glutenin molecules have the reverse effect. Thus the mean molecular weight distribution of the glutenin monomers as well as the ratio of glutenin to gliadin governs the visco-elasticity of the dough. The different foodstuffs of wheat described above require different visco-elastic properties. For example bread requires a balance of extensibility (to allow the dough to rise) and elasticity (to hold the dough volume before it sets in the oven) whereas biscuits require maximum extension (to enable thin dough sheets to be produced) and minimal elasticity (which would cause biscuit shrinkage prior to baking).

The gluten proteins of wheat are also consumed in a number of other products. Isolated gliadins have film-forming properties and are used as a surface layer or coating on confectionery to inhibit stickiness. Gliadins are further applied as a surface coating to pharmaceutical tablets for the same reason, or to inhibit the taste of unpleasant flavours during consumption of the tablet. Individuals with severe forms of coeliac disease will already be at risk from consumption of these products.

The structures of α/β-gliadins, γ-gliadins and LMW glutenin subunits are closely related and amino acid sequences are homologous in two of five sequence domains (see FIG. 1).

Nearly all LMW genes have 5 domains. The first domain containing one cystein residue is missing only in two sequences analyzed so far. Domain II, so-called repetitive domain is highly variable among the different members of LMW subfamilies. Domain III is a highly conserved domain containing 5 cystein residues found in all LMW genes. Domain IV is glutamine rich, but variable between the different subfamilies. Domain V is a conserved sequence terminating the LMWs and containing the sixth and final cystein residue. The derived amino acid sequences would result in polypeptides ranging from 33.4 to 39.5 KDa.

α- and γ-gliadins and LMW glutenins contain 6 or 8 cysteine residues that form 3 or 4 homologous intramolecular disulfide bonds. The location of these cysteine residues in the amino acid sequence is conserved among most LMW glutenin proteins. Two of the cysteine residues present in LMW glutenins form intermolecular disulfide bonds with the cysteine residues of other glutenin proteins. These 2 cysteine residues are thus responsible for the aggregative nature of LMW glutenin subunits. The structure of the storage proteins and the relevance of the cysteine residues for intermolecular crosslinking of glutenins has been analyzed in great detail in the art (Weegels and Hamer, J. Cereal Science, vol. 25 (1997), 155-163; Orsy et al., J. Biological Chemistry, vol. 276 (2001), 32322-32329; Shewry and Tatham, J. Cereal Science, vol. 25 (1997), 207-227; Lindsay et al., J. Cereal Science, vol. 31 (2000), 321-333; and Müller et al., J. Cereal Science, vol. 27 (1998), 109-116).

The use of genetic engineering methods for modifying or improving wheat gluten and wheat products has been suggested in the art. Vasil and Andersen for example suggested to modify wheat gluten by increasing the numbers of HMW-GS genes, to alter the number and position of cysteine residues, to change the physical characteristics of the gluten matrix, to change the composition and arrangement of the repeat motifs in the repetitive domain, to increase the proportion of glutenins in the large polymer fraction, to modify the polymer network, to introduce LMW-GSs with only one available cysteine for intermolecular bonds as polymer chain terminators and to modify the LMW-GSs to achieve modification of wheat quality (Trends Plant Sci., vol. 2 (1997), 292-297).

Modified glutenin genes, wherein sequences encoding a domain which confers the ability to incorporate into a gluten or bind a ligand or other macromolecule were introduced into the gene sequence, have further been reported in the art (WO00/02914).

However, so far no suggestions have been made for improving the gluten composition in such a manner that foodstuffs prepared thereof are less of a risk to patients with coeliac disease and/or other forms of gluten intolerance.

The present invention thus seeks to provide gliadin-free or gliadin-reduced foodstuff prepared from wheat, maize and/or flour derived thereof, beneficial for feeding patients suffering from coeliac disease and/or other forms of gluten intolerance, while maintaining the advantagous functional characteristics of conventional wheat, maize and/or flour containing for example wheat storage proteins.

DETAILED DESCRIPTION OF THE INVENTION

The above mentioned problem is solved by the provision of a host cell more specifically a plant cell, preferably from wheat or maize, comprising a nucleic acid sequence as set forth in SEQ ID NO: 1 and/or homologous thereof encoding a modified glutenin polypeptide as for example set forth in SEQ ID NO. 2. Said host cells comprising a sequence as set forth in SEQ.ID.NO 1 encoding a modified glutenin polypeptide, wherein the sequences encoding one or more cysteine residues responsible for intermolecular crosslinking via disulfide bridges were deleted or substituted by sequences encoding other amino acids without amending the reading frame of the coding sequence.

For sake of clarity if a cysteine residue is referred to as "a cysteine residue responsible for intermolecular crosslinking via disulfide bridges", the polypeptide containing a respective cysteine residue will form crosslinked di-, oligo- or polymers with other glutenin polypeptides containing respective cysteine residues at appropriate conditions which will allow formation of disulfide bonds, such as under the conditions obtained by expression in plant cells. Since the domain structure and the crosslinking activity of the various cysteine residues in glutenin genes are well known in the art, one of ordinary skill in the art will have no problem whatsoever to identify the cysteine residues which have to be modified or deleted in any known or newly isolated glutenin gene to result in substantially the same functionality as the current SEQ ID NO. 1 viz. providing substantially gliadin-free foodstuff prepared from cereals such as wheat, maize and/or flour derived thereof, while maintaining the advantagous functional characteristics of conventional cereals.

Alignment of different types of LMW subunits show the distribution of cysteine residues in the amino acid sequences. The distribution of the cysteine residues involved in the formation of intermolecular disulfide bonds is conserved in LMW sequences and can be used for classification of the known LMW subunit sequences.

Numerous wild type genes encoding LMW glutenins are known in the art though (Cassidy et al., Theor. Appl. Genet., 1998, 96: 743-750). Specific reference with respect to the current invention is made to the highly conserved motifs between different LMW-glutelins as mentioned in Cassidy et. al. (1998).

The glutenin genes used in the present invention differ from known sulfur rich prolamines, such as wild-type gliadin genes. Comparing the glutenin genes used in the present invention with a natural gliadin gene for example shows low (below 50%, preferably below 30%) or no homology of the genes in the 5'-end nucleotide sequence of the gene, wherein the 5'-end nucleotide sequence covers at least 15, preferably at least 30 of the nucleotides found at the 5'-end of the coding region.

In a preferred embodiment of the present invention, the used glutenin gene sequence comprises a sequence having a homology of at least 75% to the sequence shown in SEQ ID NO: 1. Preferably the sequence homology is at least 85% or at least 95% to the sequence shown in SEQ ID NO: 1. Methods for determining sequence homology are well known in the art. According to a preferred embodiment of the present invention sequence homology is determined using the BLAST Software.

The present invention is further directed to a plant preferably a transgenic plant, more specifically a cereal plant such as wheat or maize, containing plant cells wherein SEQ ID. NO 1 is integrated in the genetic material of the cell.

The transgenic plant, wheat or maize, may for example express the polypeptide encoded by SEQ ID NO 1 and depicted as SEQ. ID NO 2 in the seed and thus provide a seed containing a gliadin substitute.

Specific advantages of the present invention are obtained if the expression of at least one of the endogenous gliadin genes in the genome of a transgenic wheat plant is reduced or inhibited.

Part of the invention is the provision of transgenic plants wherein for example the expression of all endogenous gliadin genes in the genome of the plant has been reduced or inhibited and which—at the same time-express the modified glutenin polypeptide which does not contain any cysteine residues responsible for intermolecular crosslinking. The storage proteins of the seed of respective transgenic plants thus no longer contain gliadin. For the purpose of preparing foodstuffs from the seed of respective transgenic plants the modified glutenin polypeptide as depicted in SEQ ID NO 2 serves as a gliadin substitute.

Furthermore within the scope of the present invention is a transgenic plant wherein the reduction or inhibition of earlier mentioned expression comprises a modification of the cis and/or transactivating regulatory sequences and/or comprises a modification of the coding sequence of a gliadin gene and/or wherein said expression is influenced by an RNA interfering sequence or by an anti sense gliadin sequence as such.

The modification of the genes or sequences mentioned above comprises either a deletion, substitution or addition of the appropriate nucleotide sequences known to a person skilled in the art how to comply herewith.

Seed and/or products derived thereof like whole grain, wet-milled grain, starch, other protein fractions or flour, of a transgenic plant as described above is also within the scope of the current invention.

Within the scope of the present invention is a method of preparing a transformed plant cell comprising several steps wherein a plant cell is transformed with a nucleic acid sequence as set forth in SEQ ID NO 1. Transformation of plant cells is preferably used to prepare transgenic plants. Transgenic plants may for example be prepared by regeneration of transformed plants from transformed plant cells. Numerous methods for transformation of plant cells and regeneration of full fertile plants are known in the art. Transformation of plant cells are known in the art and the method used largely depends on the plant cell type used. Reference is made to among others Agrobacterium transformation and shot gun or biolistic transformation methods.

The transgenic plant may further comprise a genetic alteration, which inhibits or reduces the expression of at least one endogenous gliadin gene. The genetic alteration may be introduced before, together with or after the transformation with the nucleic acid sequence as set forth in SEQ ID NO:1.

According to a preferred embodiment of the invention all genes encoding a gliadin polypeptide are inactivated in the plant genome. This method provides cereal plants, such as wheat or maize, having seed, wherein no natural gliadin polypeptides are expressed. At the same time the modified glutenin as set forth in SEQ ID NO 2, which does not contain any cysteine residue responsible for intermolecular crosslinking is expressed as a gliadin substitute.

A thus obtained stable transformed transgenic cereal plant can, after transformation, be crossed by conventional breeding with other cereal varieties whereby the genetic means for modified low molecular weight glutenin is ultimately introgressed in elite lines for bulk production of seed for further use in the preparation of food stuff.

In addition, alternatively, a natural occuring cereal variety or a special selected variety, like a gliadin-null variety, can be used for breeding with the variety containing the desired trait obtained by the current invention.

The functionality of the cereals as used for several purposes depending on its final product can thus be restored in using those gliadin-null varieties with introgression of the trait containing the modified low molecular weight glutenin according to the invention.

In addition to restoring functionality to wheat that has been modified to reduce gliadin expression, the sequence SEQ ID. NO 1 may alternatively be expressed to varying levels in different genetic backgrounds as a tool to modulate extensibility. Such wheats have novel functionality and end use properties.

Specific advantages are obtained if seeds or other parts thereof derived from a transgenic plant are used for the preparation of foodstuff. If the transgenic plant is a cereal, one will obtain foodstuff having a significantly reduced gliadin concentration. The foodstuff may comprise dough, batters, pastries, cookies, pasta, waffers, bread and/or confectionery. Such foodstuff is better tolerated and may advantageously be consumed by patients with coeliac disease or general intolerance to wheat. The latter foodstuff has the advantagous properties of respective foodstuffs prepared from wheat or maize containing LMW glutenin subunit(s) and can be consumed by patients with coeliac disease with less or without side effects and thus addresses a long felt need, specifically in the treatment of patients with coeliac disease or general intolerance to gluten.

BRIEF DESCRIPTION OF THE FIGURES

FIG. 2: Nucleotide sequence of the modified LMW a3Δcys2gene (903 base pairs) (SEQ ID NO:1); the modified sequences are marked in bold and underlined.

FIG. 3: Amino acid sequence of modified LMW a3Δcys2 protein (297 amino acids) (SEQ ID NO:2); the modified parts are underlined.

FIG. 5: insert sequence of clone pL-Zc2T-2 (SEQ ID NO:3)

FIG. 6: pHMWz plasmid map

FIG. 7: insert sequence of clone pHMWz-4 (SEQ ID NO:4)

FIG. 8: pHMW-a3z

FIG. 9: insert sequence of clone pHMW-a3z-18 (SEQ ID NO:5)

FIG. 10: pHMW-a3$_A$2Cz

FIG. 11: insert sequence of clone pHMW-a3Δ2Cz-28 (SEQ ID NO:6)

EXAMPLES

Example 1

The GUS-reporter Gene Constructs

The uidA-reportergene construct p1.7γZGUS (Torrent et al. 1997) harbouring the maize 27 kDa γZein gene promoter was obtained from Dr. D. Ludevid (Institut Biologia Molecular Barcelona, Spain).

The construct pHMW4-GUS harbouring a High Molecular Weight glutenin gene promoter from Triticum aestivum cv. Florida in front of the uidA gene was obtained from Drs. S. Lütticke and S. Sprunck (Institut für Allgemeine Botanik, Universität Hamburg, Germany). It was cloned the following way: The High Molecular Weight glutenin promoter was amplified from genomic DNA of the wheat cv. Florida using the primers HMW1 (5'-CGAATTCGATCCTATATTAATTT-TAGACAT-3', SEQ ID NO:7) and HMW3 (5'-GCTGCA-GATATCTCGGTGGACTATCAGTGAATT-3', SEQ ID NO:8). The ends of the PCR fragment were blunted using Pfu DNA polymerase and ligated into the plasmid pCR-Script-Amp (Stratagene, La Jolla, USA) which was linearised with Srf I. From this construct the promoter was amplified with the primers M13 forward and HMW4 (5'-GGCCGCTCTAGC-CGAATTCATCTCGGTGGACTA-3', SEQ ID NO:9). This PCR product was cut with EcoR I and ligated into pBluescript KS+ (Stratagene, La Jolla, USA), which was also linearised with EcoR I, yielding the construct HMW4/Eco. The promoter was isolated from HMW4/Eco as an EcoR I fragment, blunted with mung bean nuclease and ligated into the plasmid gusnos630 (pBluescript SK- harbouring the uidA-nos terminator fragment from the plasmid CalGUS (Callis et al. 1987)), which was cut with Nco I and blunted with mung bean nuclease. This resulted in the plasmid pHMW4-GUS.

Figure 16:
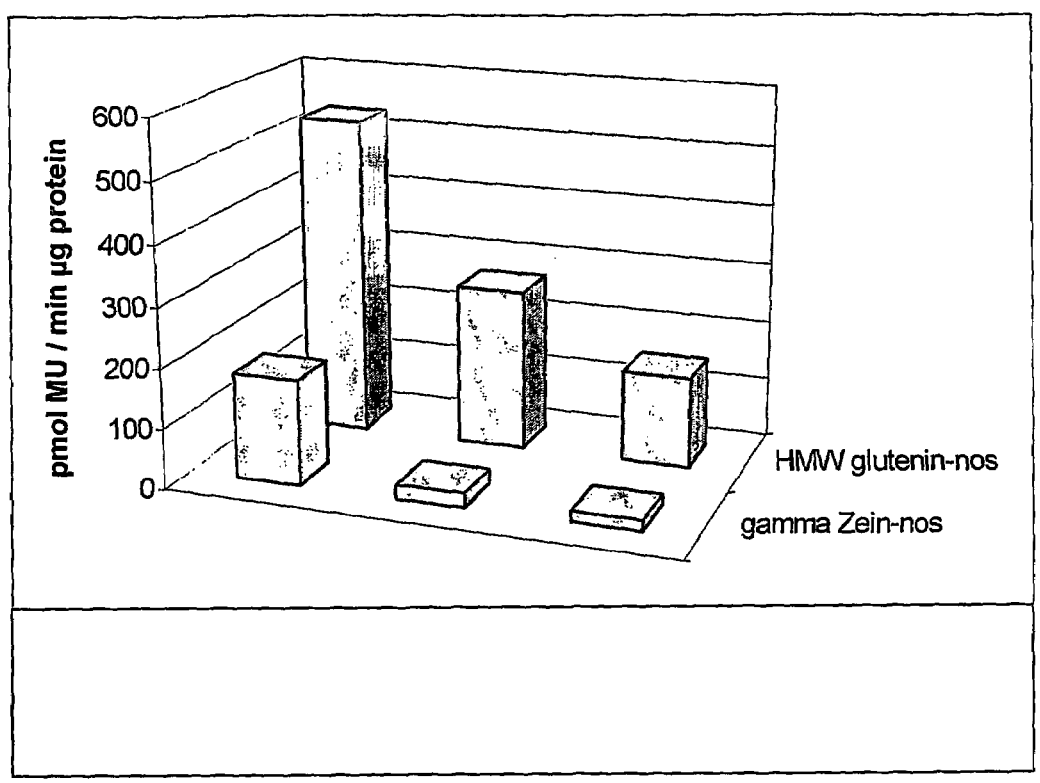
FIG. 16: Comparison of the β-glucuronidase activity in maize endosperm, when driven by either the HMW glutenin promoter or the 27 kDa γ-Zein promoter. From each transformation experiment data from the three strongest expressing lines are represented.

In order to evaluate the strength of expression generated by the two endosperm specific promoters High Molecular Weight glutenin promoter and 27 kDa γ Zein promoter, thus finding which of these is more suitable for the high level expression of recombinant storage proteins in maize endosperm, maize was transformed with the respective uidA reporter gene constructs p1.7γZGUS and pHMW4-GUS respectively. Endosperm representing the T1 generation was analyzed for the amount of β-glucuronidase activity. It was found that the expression driven by the HMW glutenin promoter is at least three times as much as the one driven by the γ Zein promoter (FIG. 16). Therefore the HMW glutenin promoter was chosen for the construction of the storage protein gene expression constructs.

Histochemical and Fluorometric Analysis of β-glucuronidase Activity

Histochemical and fluorometric analysis of β-glucuronidase activity was essentially performed as described by Jefferson et al. (1987). T0 plants were pollinated with pollen from the inbred line A188. Twenty-eight dap, from each cob 20 kernels, representing the T1 generation were tested histochemically for GUS activity: After surface sterilisation the embryos were removed from the kernels, which then were cut in half. Subsequently one half of each kernel was subjected to the histochemical GUS assay. On an average eight kernels, which showed GUS activity in the endosperm and two kernels, which did not as a negative control, were used to quantify GUS activity fluorometrically: Protein extracts from the second halves of the respective kernels were used in the fluorometric assay, deploying a Fluoroscan II fluorimeter (Labsystems) with 4-methylumbiliferone as a standard according to the manufacturer's instructions.

Construction of LMW Glutenin a3 and LMW Glutenin a3Δ2C Expression Plasmids:

The expression constructs are based on the plasmid litmus38 (New England Biolabs, Beverly, Mass., USA). 589 bp from the 3' UTR of the 27 kDa γZein Zc2 from maize (Reina et al., 1990: Sequence analysis of a genomic clone encoding a Zc2 protein from Zea mays W64 A. Nucl. Acids Res., 18, 6426) were amplified by PCR from the plasmid p2-16, which harbours the respective sequence from the imbred line A188.

The oligonucleotides γZT5'-BamHI (5'-GCTCGGATC-CCCTAGGTACCTGAAGAAACTATGTGCT-GTAGTATAGCC-3', SEQ ID NO:10) and γZT3'-SfiI (5'-GCTCTGTACAGGCCCTTAAGGCCGCTTCAAGTCTTT AACTAAGGGAGG-3', SEQ ID NO:11) were used for the PCR reaction.

Figure 1:
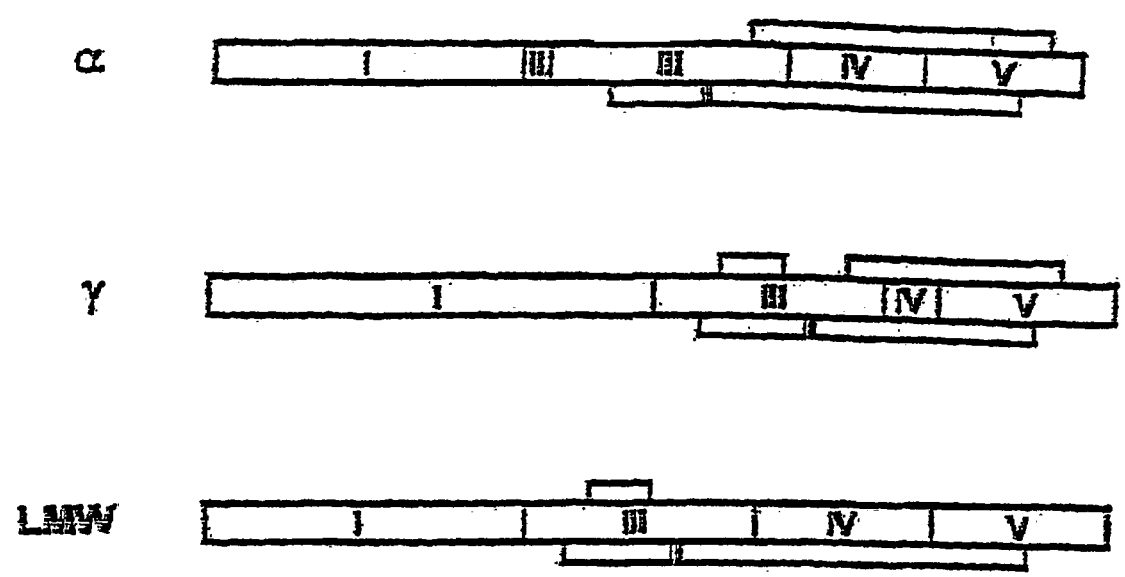
FIG. 1: Schematic diagram comparing the domain structure and showing the disulfide bridges of α-gliadin, γ-gliadin and LMW subunits of glutenin.
Figure 4:
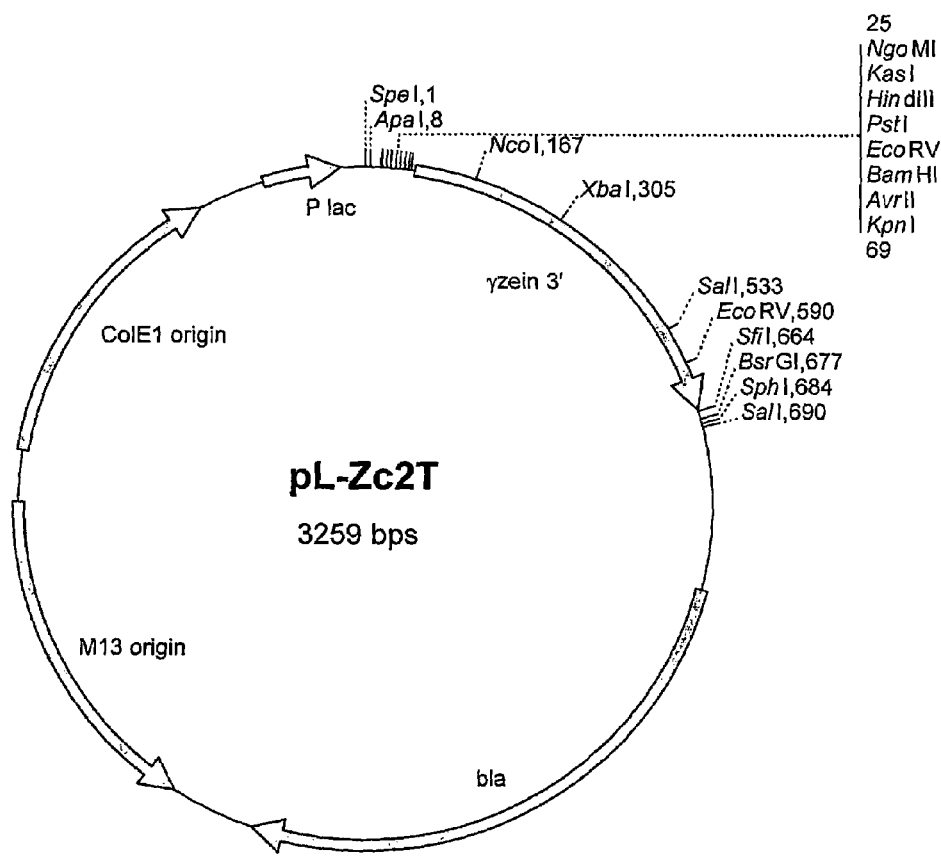
FIG. 4: pL-Zc2T plasmid map

The PCR product was ligated with T4 DNA ligase (Invitrogen GmbH, Karlsruhe, Germany) into litmus38 taking advantage of the BamHI and BsrGI restriction sites, yielding the plasmid pL-Zc2T (FIG. 4). The insert of the clone #2 was sequenced (FIG. 5). The sequence differs in some nucleotides from the published one, which is from line W64 A (Acc. no: X53514).

718 bp from the region upstream of the start-ATG of a High Molecular Weight (HMW) glutenin gene from the German wheat cultivar Florida were introduced into pL-Zc2T in front of the γZein 3' UTR: The promoter was amplified by PCR from the plasmid pHMW4-GUS using the oligonucleotides HMW_5'-SfiI (5'-GCTCGGGCCCGGCCATGGCGGC-CGAATTCGATCCTATATTAATTTT-3',SEQ ID NO:12) and HMW_3'-NdeI (5'-CAGTGGATCCCATATGCTCGG-TAGGACTATCAGTGAATT-3', SEQ ID NO:13) and ligated with T4 DNA ligase (Invitrogen GmbH, Karlsruhe, Germany) into pL-Zc2T taking advantage of the ApaI and BamHI restriction sites. This resulted in the plasmid pHMWz (FIG. 6). The sequence of the insert of clone #4 was confirmed. (FIG. 7)

The cDNAs of the Low Molecular Weight (LMW) glutenin a3 and its modified version a3Δ2C were introduced in pHMWz between the HMW glutenin promoter and the γZein 3' UTR: The two cDNAs were amplified by PCR from the plasmids pBluescript-LMWa3 and YpADH-LMWa3Δcys2 respectively using the oligonucleotides LMWa3_5' (5'-AG-ATCCGTACATATGAAGACCTTCCTCGTCTTTGCC-3', SEQ ID NO:14) and LMWa3_3' (5'-GCTATCTAGAT6CAGTAGGCACCAACTCGGCTGCC-3', SEQ ID NO:15) and then ligated with T4 DNA ligase (Invitrogen GmbH, Karlsruhe, Germany) into pHMWz using the NdeI and AvrII/XbaI restriction sites, taking advantage of the compatible overhangs of cleaved AvrII and XbaI sites. This resulted in the expression plasmids pHMW-a3z (FIG. 8) and pHMW-a3Δ2Cz (FIG. 10). The sequences of the inserts of both plasmids were determined. In clone pHMW-a3z-18 the sequence of the introduced LMWa3 reading frame differs in 1 base pair (G153A) from the original sequence, which does not lead to a change in the coded amino acid (FIG. 9). The resulting nucleotide sequence of the reading frame is identical to the one published with the accession number AB062873. The nucleotide sequence of the insert of clone pHMW-a3Δ2Cz-28 (FIG. 11) is identical to the one in the plasmid YpADH-LMWa3Δcys2.

Example 2

Production of Wheat Plants which Express a Modified LMW Gene from *Triticum aestivum*.

The biolistic transformation method is used for the production of wheat (Becker et al., Plant J. 5(2), 1994, 229-307). The vector pHMW-a3Δ2Cz and, for biolistic cotransformation, the vector pAct1-Fneo (Müller et al., Plant Science 114, (1996), 71-82) are used in identical molar ratios in the DNA particle precipitation batch. Scutelli from 14-day old, unripe zygotic embryos of wheat plants were used as target cells for transformation. Transformation was followed by in vitro culture on MS⁻ medium (PCT/EP97/02793) containing 2 mg/l 2,4-D (=2,4-dichlorophenoxyacetic acid). Two weeks after transformation, subculture is effected on the same medium, to which 150 mg/l kanamycin sulphate is added. After a further two weeks, the developing calli are transplanted on to a regeneration medium (MS⁻ medium with 0.1 mg/l 2,4-D and 150 mg/l Kanamycin). The developing shoots are transferred to semi-concentrated MS⁻ medium without 2,4-D and kanamycin and are subsequently transferred into the ground. About 14 days after their establishment in the ground, the transgenic plants are identified by spraying twice with an aqueous solution containing 2.5 and 3.0% Kanamycin sulphate, 0.1% Tween20.

Example 3

Production of Maize Plants which Express a Modified LMW Gene from *Triticum aestivum*

Figure 12:
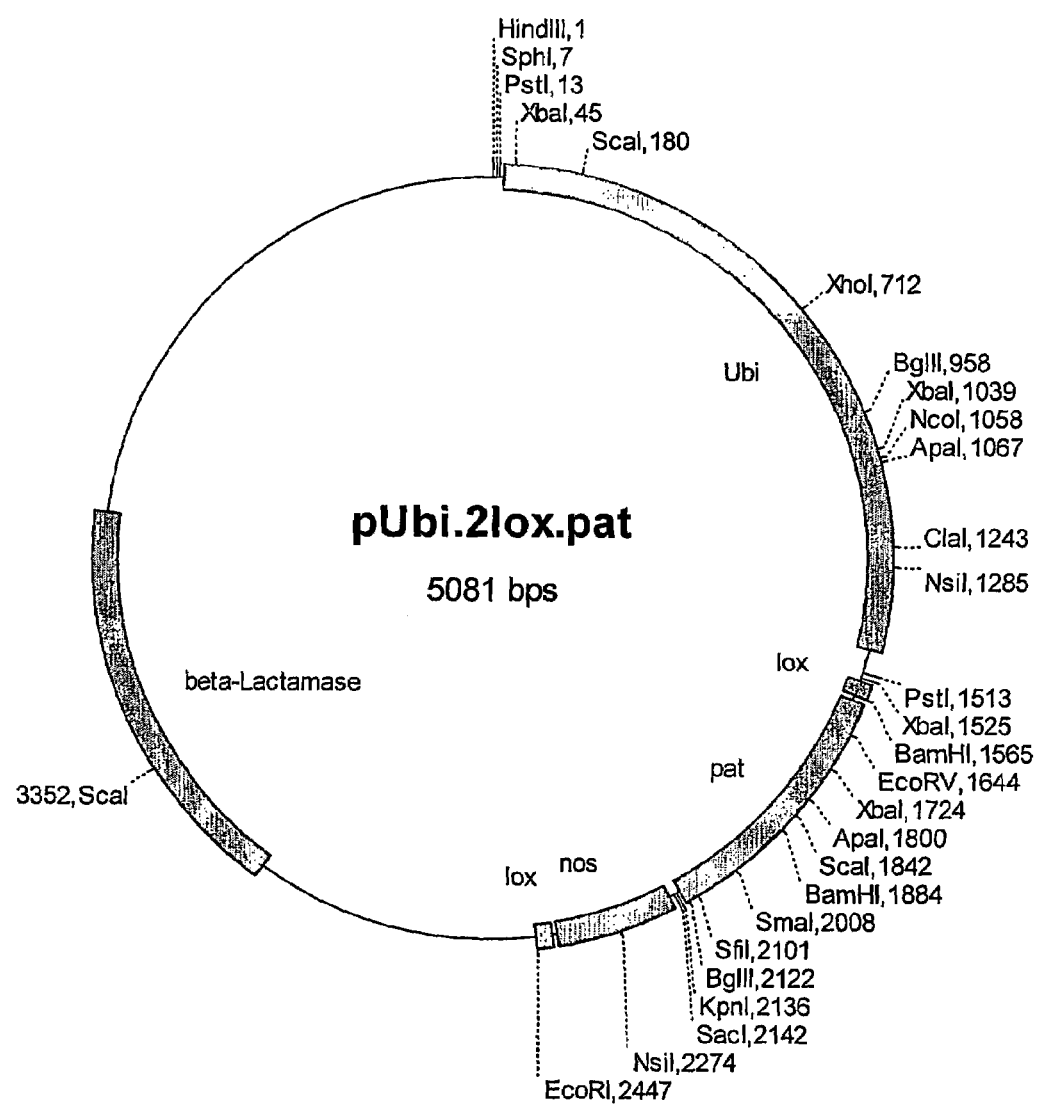
FIG. 12: pUbi.2lox.pat plasmid map
Figure 13:
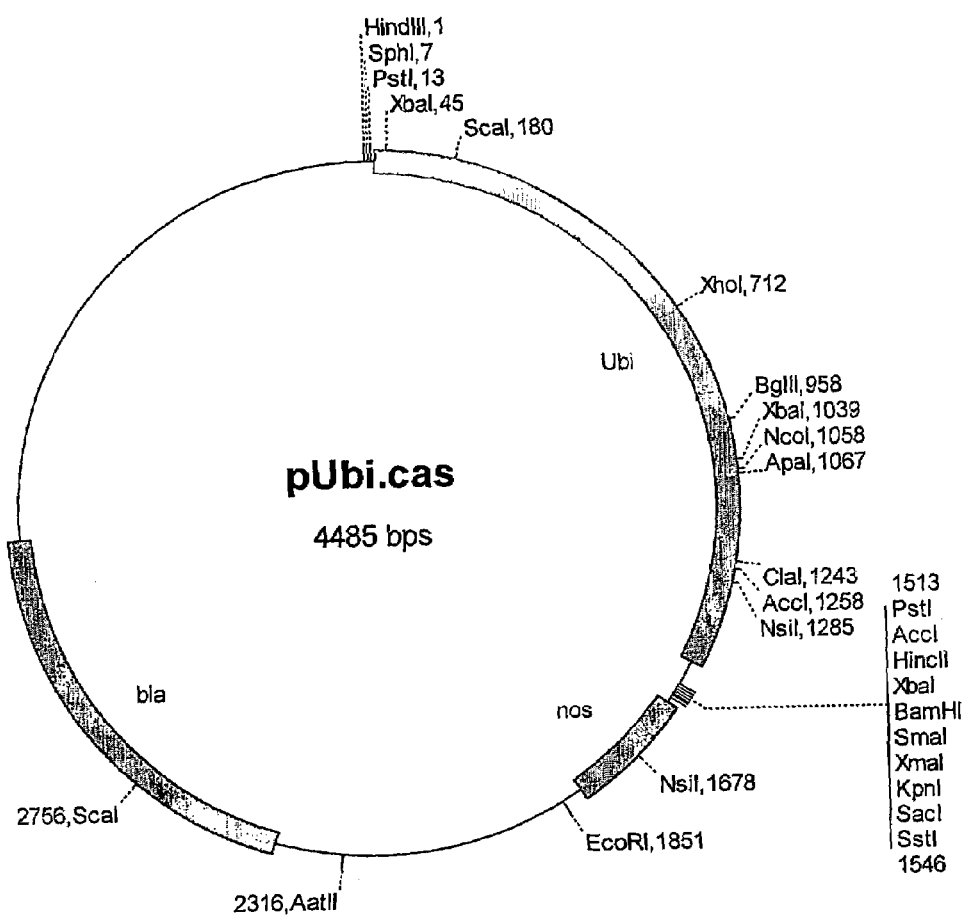
FIG. 13: pUbi.cas plasmid map
Figure 14:
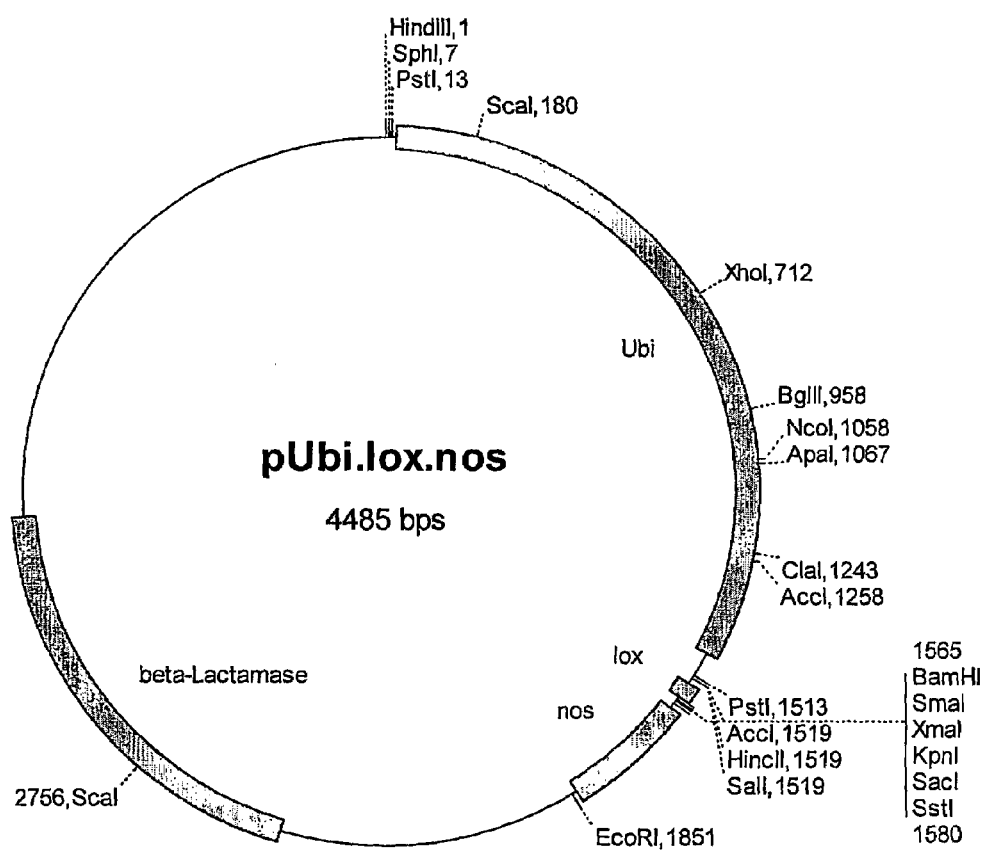
FIG. 14: pUbi.lox.nos plasmid map
Figure 15:
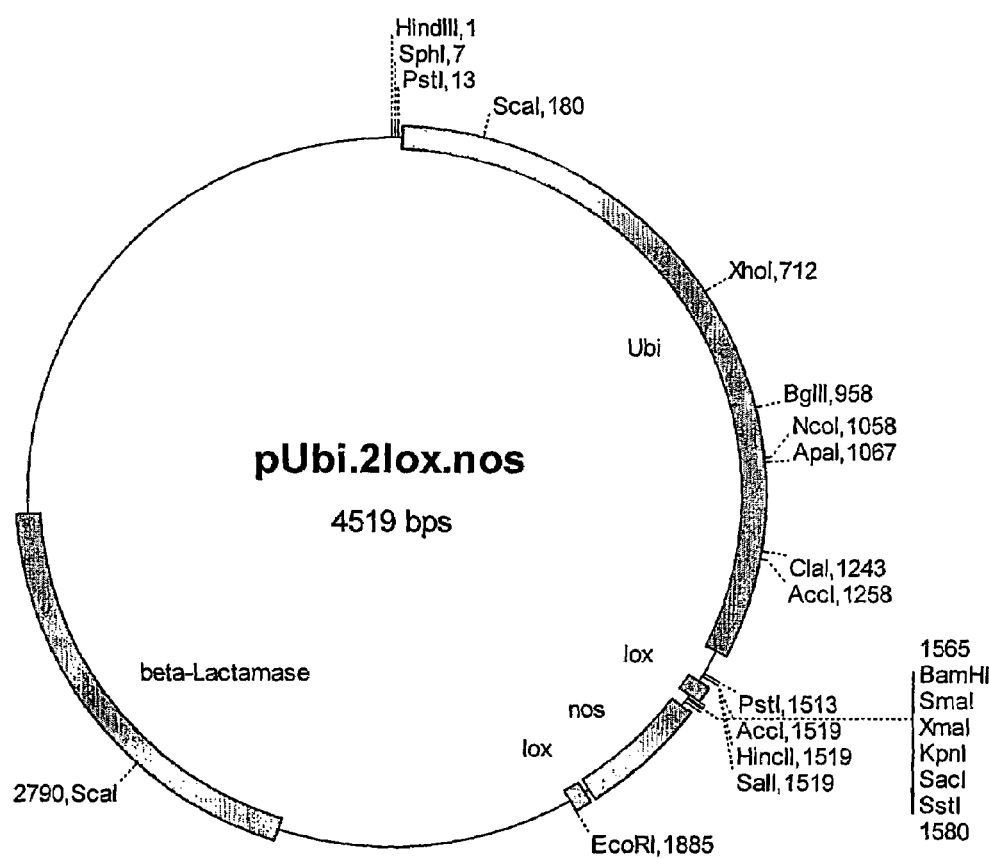
FIG. 15: pUbi2lox.nos plasmid map

The biolistic transformation method is used for the production of maize (Brettschneider et al., 1997, Theor. Appl. Genet 94, 737-748). The vector pHMW-a3Δ2Cz and, for biolistic cotransformation, the vector pUbi2loxPAT (FIG. 12) are used in identical molar ratios in the DNA particle precipitation batch. Vector pUbi.2lox.pat was produced as follows: The loxP sequences are introduced into the cloning vector pUbi.cas (FIG. 13) by PCR. The vector pUbi.cas contains the pUC19 vector (Yannish-Perron et al., 1985, Gene 33: 103-119), the 1,5 Kb ubiquitin promoter and the first exon of the ubi gene and a shortened ubiquitin1 intron (ClaI deletion) (Christensen et al., Plant Mol. Biol. 18, (1992), 675-689) and the 250 bp nos-terminator from *Agrobacterium tumefaciens* nopalin synthase gene. The loxP sequences are localised 3' from the Ubiquitin promoter and 3' from the nos-terminator sequences. Following PCR primers were used: P1: 5'TCCG-GTCCATGGTTAGGGCCC3' (SEQ ID NO:16) and lox2: 5'CCCGGGGATCCATAACTTCGTATAATG-TATGCTATACGAAGTTATTCTAGAGTCGA CCTGCA-GAGTAACACCAAAC3' (SEQ ID NO:17) for the lox P side creation behind the 3' end of the Ubiquitin promoter. The template DNA for amplification was the cloning vector pUbi-.cas. The PCR Fragment was digested with NcoI/BamHI and ligated into the NcoI/BamHI digested pUbi.cas vector to create the vector pUbi.lox.nos (FIG. 14). The second loxP side, located 3' of the nos terminator was introduced by PCR amplification and ligation into pUbi.lox.nos using the following primer: P3 5'GGTACCGAGCTCGAATTTCCCCGATCGT-TCAAACATTTGGC3' (SEQ ID NO:18) and lox4 5' TAG-TACGAATTCATAACTTCGTATAATGTAT-GCTATACGAAGTTATCCGATCTAGT AACATAGATGACACCGCGC3' (SEQ ID NO:19) and as template DNA pUbi.lox.nos digested with EcoRI/Hind III. The PCR fragment was digested with SstI/EcoRI and ligated into pUbi.lox.nos vector digested with the same restriction enzymes. The resulting construct was designated as pUbi.2lox.nos (see FIG. 15).

The resulting construct pHMW-a3Δ2Cz (FIG. 10) was used to transform, via a modified particle bombardment protocol (Brettschneider et al. 1997, Theor. Appl. Genet 94, 737-748), scutellar tissue of immature embryos of the hybrid maize line A188xH99. The vector pHMW-a3Δ2Cz and, for biolistic cotransformation, the vector pUbi.2lox.pat are used in identical molar ratios in the DNA particle precipitation batch.

1.0-1.4 mm long immature zygotic embryos were isolated and cultured on N6.1.100.25 (N6) nutrient medium (Songstad D. D., Petersen W. L., Armstrong C. L. (1992). Am. J. Bot. 79, 761-764). The modifications to the original protocol from Brettschneider et al. (1997) are:

a) Freshly isolated embryos were cultured for one day on N6 sucrose medium with an osmotic value of 700 mOsm. Next day, embryos are subcultured on normal N6.1.100.25 medium supplemented with 1 mg/l 2,4-D for 5-12 days before microprojectile bombardment.

b) The BASTA selection was started 14 days after bombardment when the calli were subcultured on N6.1.100.25 medium, supplemented with 1 mg/l 2,4-D and 1 mg/l PPT (Phosphinothricin), the active compound of the commercial herbicide Basta. During herbicide selection, all media were preparated without casamino acids c) All media were solidified with Phytagel instead of Agarose.

Example 4

Herbicide- and Antibiotic Application

All regenerants from the selection experiments as well as progeny were sprayed two to three times with an aqueous solution of BASTA containing 250-300 mg/l phosphinothricin, 0,1% Tween 20 (maize) or 2.5-3% kanamycin, 0.1% Tween 20 (wheat). Surviving plants were further grown to maturity in the glasshouse. Plants which were transgenic for the selectable marker genes were further characterised by Southern- and Western blot analysis and by HPLC for the presence and expression of the wheat seed storage proteins, especially for the integration and expression of the LMW and modified LMW genes.

Integration and Expression of the LMW and Modified LMW Genes in $T_0$ Plants

Integration and expression of the LMW- and modified LMW genes in transgenic plants was detected by Southern-, Western blotting and by HPLC (Wieser et al. 1998). LMW and modified LMW protein was detected in the transgenic seed protein preparations 4 weeks after pollination with the aid of polyclonal antibodies.

Southern Blot Analysis

Total genomic DNA was isolated from leaf tissue with a rapid extraction protocol (Palotta et al. 2000). Uncut and restriction enzyme-digested genomic DNA (15 µg per lane) or 20 pg of restricted plasmid DNA (positive control) were separated in a 0.8% agarose gel, blotted onto a Hybond NX nylon membrane (Amersham, Braunschweig, Germany), and hybridized to 32P-labeled probes synthesized from DNA restriction fragments with the Deca Label DNA labeling Kit (MBI Fermentas, St. Leon-Rot, Germany). Non incorporated nucleotides were removed with Microspin columns HR S300 (Pharmacia, Erlangen, Germany), and hybridization was carried out as described (Sauter 1997). Blots were washed successively at 68° C. for 10 min in 2×SSC, 0,1% SDS; 0,5×SSC, 0,1% SDS and 0,2×SSC, 0,1% SDS.

Protein Extraction

For one-dimensional SDS-PAGE endosperm from seeds were ground using a mortar and pestle in 2×PBS (PBS=10 mM phosphate buffer, pH 7.4, 140 mM sodium chloride) (1 ml per 2 g FW). After centrifugation (20100×g, 15 min, 4° C.) the protein content in the supernatant was determined according to Bradford (1976). Depending on the protein concentration an equal volume of 2×SDS sample buffer (Laemmli, 1970) was added.

Electrophoresis

One-dimensional electrophoresis was performed according to Laemmli (1970). The gel concentration was between 6-12%. Either 13 or 3 µg of protein per lane were loaded onto minigels (8×10 cm) followed by Comassie or silver staining or for Western blot analysis, respectively. Western blotting was performed according to Albrecht et al. (1998).

Production of Progeny from Transgenic Maize Plants.

Progeny plants were produced from mature seeds in the glasshouse or by embryo rescue. Therefore, immature embryos were isolated from immature seeds 4 weeks after pollination.

Seeds were surface sterilized (1% sodium hypochloride, 0.5% Mucasol) for 20 min and washed three times with sterile distilled water. Embryos were excised from the seeds under aseptic conditions and placed with the scutellum in contact to solidified (0,4% agarose) MS-medium without phytohormons (Murashige and Skoog, 1962).

Example 5

Dough Production for Micro-Baking Test

For micro-baking tests, 10 g maize flour, 0.2 g NaCl, 0.4 g glucose, 0.7 g fresh bakery yeast, and 2 ml of $H_2O$ were mixed for 2 min at 22° C. in the Farinograph. The dough was put in little pans coated with Teflon and allowed to stand for 40 min at 30° C. The baking time was 10 min at 240° C.

Example 6

Expression of a Low Molecular Weight Glutenin Subunit and its Modified Variant in the Endosperm of Maize Preparation of Storage Protein Extracts from Maize Endosperm Four week old embryos were isolated from the kernels and transferred under sterile conditions onto MS media. The remaining kernel was stripped of the pericarp and frozen in liquid nitrogen and stored away for further processing at −70° C. For the extraction of storage proteins, endosperms from which the respective seedling had been tested positive for the transgene by PCR were handled the following way: the endosperms were ground under liquid nitrogen. Then approximately one third of each sample was extracted two times with 0.5 mL 0.4 mol/L NaCl, 0.067 mol/L $HKNaPO_4$, pH 7.6 for 10 min while stirring at room temperature. After each extraction the samples were centrifuged at 13000 rpm for 7 min at room temperature. The supernatants were discarded and the samples were then extracted two times with 0.5 mL 50% (v/v) 2-propanol, 2 mol/L urea, 0.05 mol/L Tris-HCl, pH 7.5, 1% (w/v) DTT for 20 min while stirring at 60° C. Here again the samples were centrifuged at 13000 rpm for 7 min at room temperature. The supernatants of each sample were collected and then dried in a centrifuge concentrator and resuspended in 100 µl SDS-PAGE sample buffer (Laemmli 1970).

SDS-Polyacrylamide Gel Electrophoresis

Five µl of the samples were loaded onto a 12% SDS-PAGE-mini gel, which was prepared according to Laemmli (1970). After the gel run the gel was stained in 50% (v/v) methanol, 10% (v/v) acetic acid and 0.25% (w/v) Coomassie Brilliant Blue R-250 for 1 hour. The gel was destained in 5% (v/v) methanol, 7.5% (v/v) acetic acid for several hours.

Results

Figure 17:
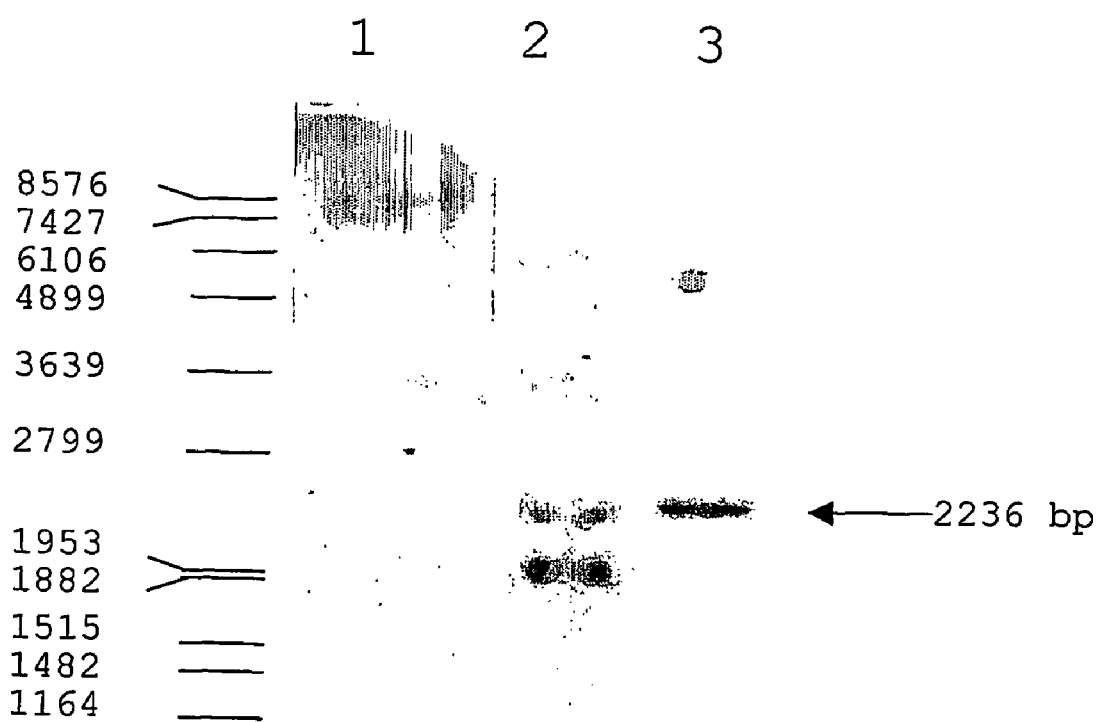
FIG. 17: Southern blot of genomic DNA from maize line EC7-2, digested with Sfi I, and probed with a labeled HMW glutenin subunit promoter fragment.: 1: 15 µg of genomic DNA of maize inbred line A188, untransformed; 2: 15 µg of genomic DNA from line EC7-2; 3: 12 pg of the plasmid used for transformation: pHMW-a3z. Sfi I releases the entire expression cassette (HMW::LMWa3::γzein) of 2236 bp from the plasmid pHMW-a3z. The molecular weight marker VII from Roche is indicated on the left.
Figure 18:
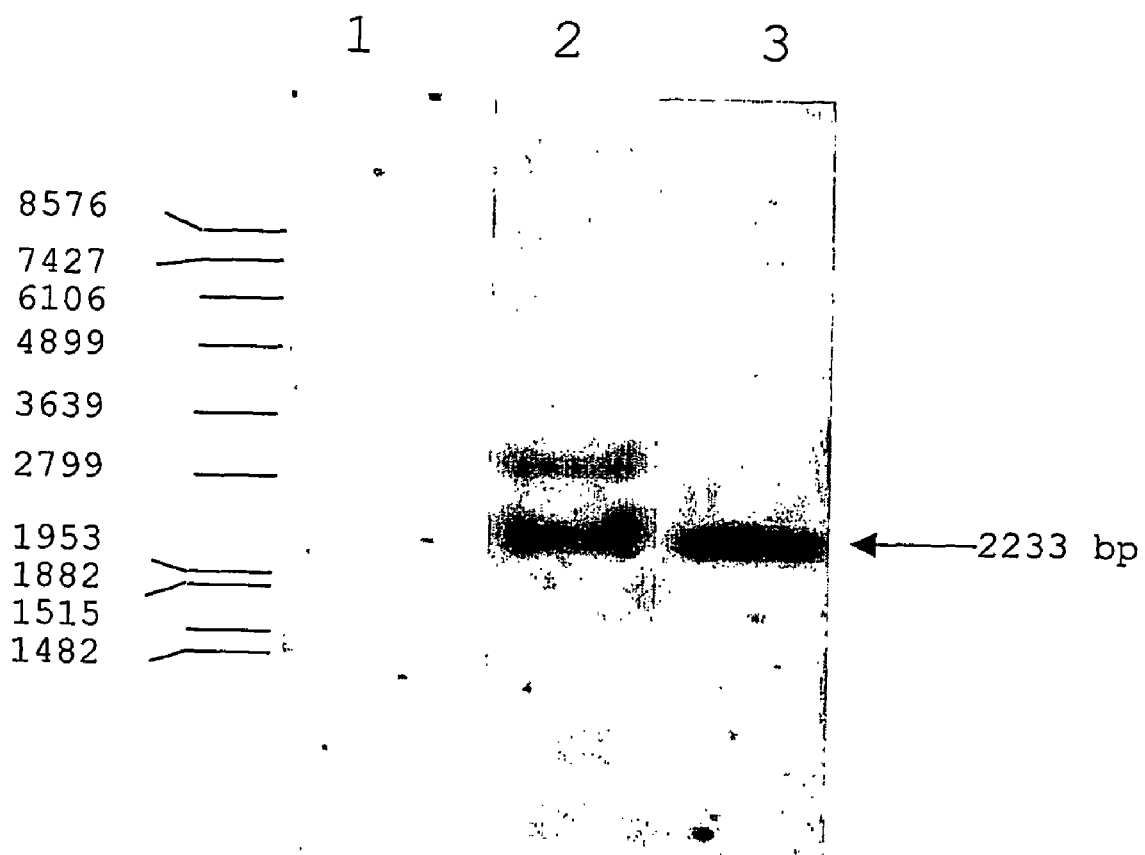
FIG. 18: Southern blot of genomic DNA from maize line ED7-2, digested with Sfi I, and probed with a labeled HMW glutenin subunit promoter fragment.: 1: 15 µg of genomic DNA of maize inbred line A188, untransformed; 2: 15 µg of genomic DNA from line ED7-2; 3: 12 pg of the plasmid used for transformation: pHMW-a3Δ2Cz. Sfi I releases the entire expression cassette (HMW::LMWa3Δ2C::γzein) of 2233 bp from the plasmid pHMW-a3Δ2Cz. The molecular weight marker VII from Roche is indicated on the left
Figure 19:
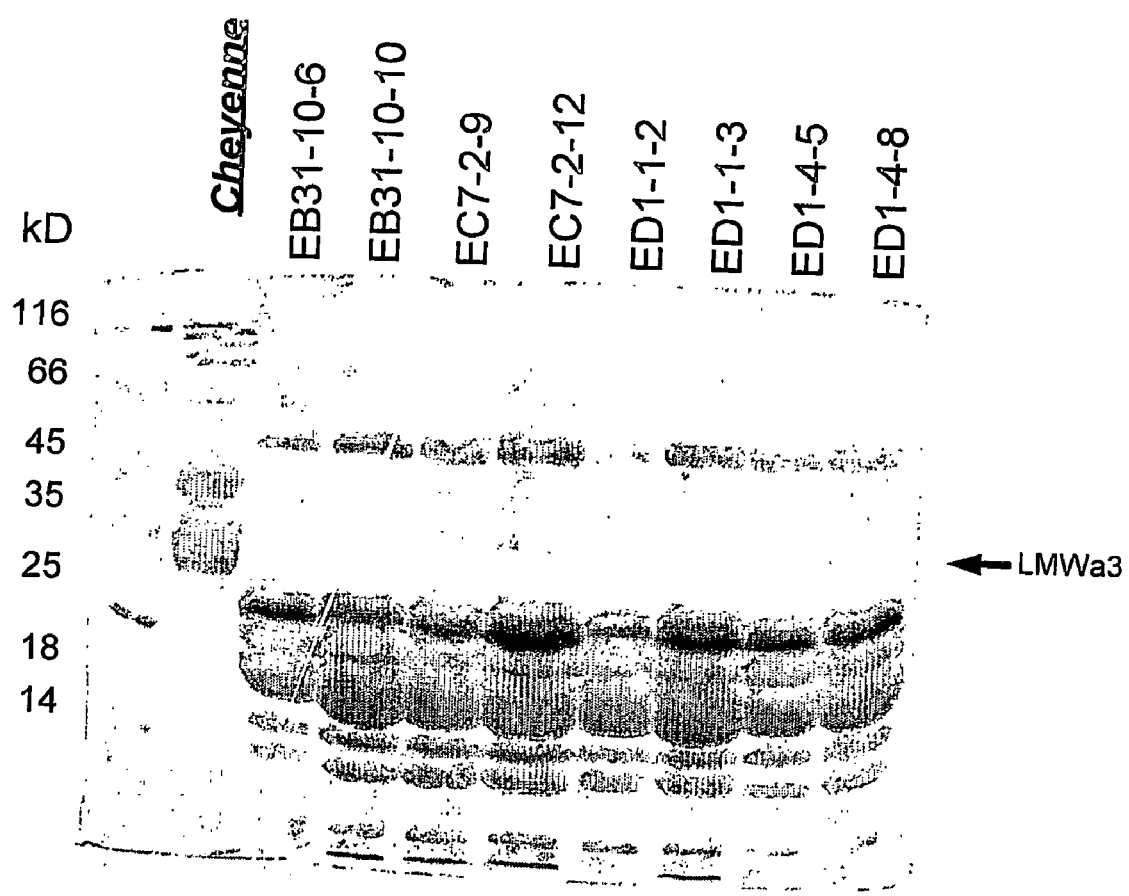
FIG. 19: Detection of the LMW glutenin subunit a3 in 2-propanol extracts from endosperms of the line EC7-2. 12% polyacrylamide gel electrophoresis stained with Coomassie Brilliant Blue. The gel shows 2-propanol extracts from endosperms (28 dap) of different lines transformed with different wheat storage protein expression constructs. Cheyenne: 2-propanol endosperm extracts from wheat cv. Cheyenne as a control; EB: transformed with an expression construct for HMW subunit 1 Dy10; EC: transformed with an expression construct for LMWa3; ED: transformed with an expression construct for LMWa3Δ2C.
Figure 20:
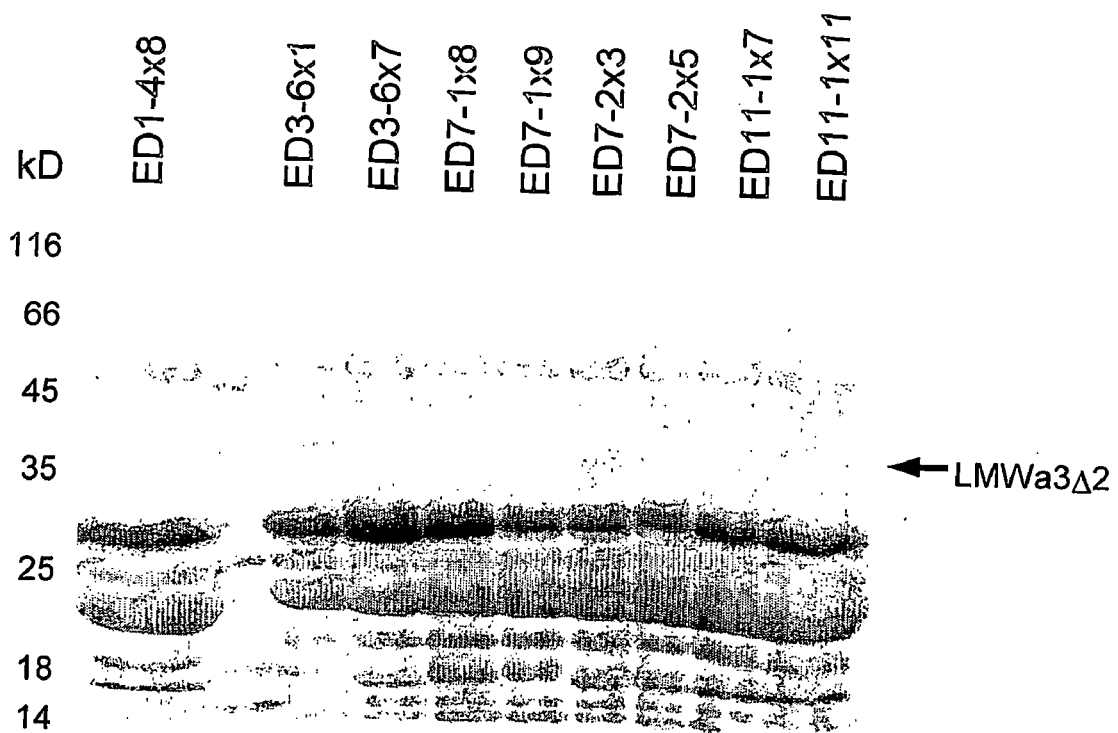
FIG. 20: Detection of the LMW glutenin subunit a3Δ2C in 2-propanol extracts from endosperm of the line ED7-2. 12% polyacrylamide gel electrophoresis stained with Coomassie Brilliant Blue. The gel shows 2-propanol extracts from endosperms (28 dap) of different lines transformed with the plasmid pHMW-a3Δ2Cz.

By 'biolistically' transforming in mature embryos of the maize hybrid A188xH99 with expression constructs for the Low Molecular Weight (LMW) glutenin a3 (pHMW-a3z) or its modified variant (pHMW-a3Δ2Cz), both under a High Molecular Weight (HMW) glutenin subunit promoter from wheat cultivar 'Florida', it was shown to generate transgenic maize lines harbouring the respective full-length expression cassettes in their genomes. This was shown by genomic Southern blot analysis: The full length expression cassettes were cut from genomic DNA, using the Sfi I restriction endonuclease, and probing the respective blots with a labelled HMW promoter sequence revealed the presence of full length fragments of the same size as in the respective plasmid controls (FIGS. 17 and 18). The lines EC7-2 and ED7-2 are expressing the respective, encoded proteins specifically in the endosperm, as was shown by SDS-polyacrylamide gel electrophoresis of 2-propanol extracts from transgenic endosperms of the T1 generation: The mature LMWa3 subunit has a predicted molecular mass of 31.77 kD and the modified variant of 31.62 kD. The apparent molecular mass according to the SDS polyacrylamide gel electrophoresis is in very good agreement with the predicted values (FIGS. 19 and 20), thereby showing that LMW glutenin subunits were successfully expressed in the endosperm of maize.

REFERENCES

Albrecht, T., Greve, B., Pusch, K., Kossmann, J., Buchner, P., Wobus, U. and Steup, M. (1998) Homodimers and heterodimers of Pho1-type phosphorylase isoforms in *Solanum tubersosum* L. as revealed by sequence-specific antibodies. Eur. J. Biochem., 251, 343-352.

Bradford, M. M. (1976), A rapid and sensitive method for the quantification of microgram quantities of protein utilising the principle of protein-dye binding. Anal. Biochem., 72, 248-254.

Callis, J., Fromm, M. E., Walbot, V. 1987. Introns increase gene expression in cultured maize cells. *Genes Dev.* 1: 1183-1200.

Jefferson, R. A., Kavanagh, T. A., Bevan, M. W. 1987. GUS fusions: β-glucuronidase as a sensitive and versatile gene fusion marker in higher plants. *EMBO J.* 6: 3901-3907.

Laemmli, U. K. (1970). Cleavage of structural proteins during the assembly of the head of bacteriophage T4. Nature, 227, 680-685.

Murashige, T and Skoog, F. (1962) A revised medium for rapid growth and bioassays with tobacco tissue cultures. Physiol. Plant., 15, 473-497.

Palotta, M. A., Graham, R. D., Landgridge, P., Sparrow D. H. B., Barker, S. J. (2000). RFLP mapping of manganese efficiency in barley. Theor. Appl. Genet., 101: 1100-1108.

Sauter, M (1997). Differential expression of a CAK (cdc2-activating kinase)-like protein kinase, cyclins and cdc2 genes from rice during the cell cycle and in response to gibberellin. Plant J. 11: 181-190.

Torrent, M., Alvarez, I., Geli, M. I., Dalcol, I., Ludevid, D. 1997. Lysine-rich modified γ-zeins accumulate in protein bodies of transiently transformed maize endosperms. *Plant Mol. Biol.* 34: 139-149.

Wieser, H., Antes, S. and Seilmeier, W. (1998). Quantitative determination of gluten protein types in wheat flour by reversed-phase high-performance liquid chromatography. Cereal Chem., 75, 644-650

The invention claimed is:

1. A plant cell comprising a nucleic acid sequence as set forth in SEQ ID NO:1 or a homologous sequence thereof, wherein the homologous sequence encodes SEQ ID NO:2.

2. A transgenic plant comprising the plant cell according to claim 1.

3. The transgenic plant according to claim 2, wherein the plant is a cereal plant.

4. The transgenic plant of claim 3, wherein the plant is a wheat or maize plant.

5. A seed or product thereof, wherein said seed is from the transgenic plant according to any one of claims 2, 3 or 4, and wherein said seed or product thereof comprises SEQ ID NO:1 or a homologous sequence thereof that encodes SEQ ID NO:2.

6. A method of preparing foodstuff comprising the step of processing the seed of claim 5.

7. The method of claim 6, wherein flour is obtained from the processing step and is used for the preparation of dough, batters, pastries, cookies, pasta, wafers, bread or confectionery.

8. The method of claim 6, wherein the foodstuff is tolerable to individuals having coeliac disease or a general intolerance to gluten.

* * * * *